(12) United States Patent
Taki et al.

(10) Patent No.: US 11,474,378 B2
(45) Date of Patent: Oct. 18, 2022

(54) TEST METHOD PERFORMED USING LENS

(71) Applicant: TOYODA GOSEI CO., LTD., Kiyosu (JP)

(72) Inventors: Seitaro Taki, Kiyosu (JP); Yasuhiko Shinoda, Kiyosu (JP); Hiroyuki Nakagawa, Kiyosu (JP); Rie Kimura, Nagoya (JP)

(73) Assignee: TOYODA GOSEI CO., LTD., Aichi-pref. (JP)

( * ) Notice: Subject to any disclaimer, the term of this patent is extended or adjusted under 35 U.S.C. 154(b) by 973 days.

(21) Appl. No.: 16/225,188

(22) Filed: Dec. 19, 2018

(65) Prior Publication Data

US 2019/0196222 A1 Jun. 27, 2019

(30) Foreign Application Priority Data

Dec. 27, 2017 (JP) .............................. JP2017-250516

(51) Int. Cl.
*G02C 7/02* (2006.01)
*G02C 7/08* (2006.01)
(Continued)

(52) U.S. Cl.
CPC ......... *G02C 7/027* (2013.01); *G01M 11/0207* (2013.01); *G01M 11/0214* (2013.01);
(Continued)

(58) Field of Classification Search
CPC .......... G02C 7/085; G02C 7/02; G02C 7/027; G02C 7/04; G02C 7/049; G02C 7/086; G02C 2202/18; A61F 2/1601; A61F 2/16; G01M 11/02; G01M 11/0207; G01M 11/0214; G01M 11/0285; G01N 21/75
See application file for complete search history.

(56) References Cited

U.S. PATENT DOCUMENTS 6,454,802 B1 * 9/2002 Bretton .................. A61L 27/50
623/6.62
2002/0049389 A1 * 4/2002 Abreu ...................... G02C 7/04
600/318
(Continued)

OTHER PUBLICATIONS

"Safety of color contact lenses for fashion (Overview)-for not aiming at vision correction," Feb. 3, 2006, National Consumer Affairs Center of Japan (searched on Dec. 5, 2017) www.kokusen.go.jp/pdf/n-20060203_1.pdf (and English machine translation).
(Continued)

*Primary Examiner* — Jordan M Schwartz
(74) *Attorney, Agent, or Firm* — Posz Law Group, PLC

(57) ABSTRACT

Provided is a test method performed using a lens which comes into contact with a human body during use, the test method including the steps of: providing a membrane member including a membrane swellable upon absorbing water and a supporting base having an annular shape to support an outer periphery of the membrane; allowing cells to adhere on the membrane of the membrane member; and bringing the membrane to which the cells are adhered into close contact with the surface of the lens, by immersing the membrane member and the lens into a liquid and deforming the membrane in a swollen state along the surface of the lens.

13 Claims, 17 Drawing Sheets

(51) Int. Cl.
*G01M 11/02* (2006.01)
*G02C 7/04* (2006.01)
*G01N 33/50* (2006.01)
*A61B 3/107* (2006.01)

(52) U.S. Cl.
CPC .......... G01N 33/5008 (2013.01); G02C 7/04 (2013.01); G02C 7/085 (2013.01); *A61B 3/107* (2013.01); *G01N 2333/00* (2013.01)

(56) References Cited

U.S. PATENT DOCUMENTS

2010/0074942 A1* 3/2010 Ratner ................. A61K 31/711
 29/282
2015/0342725 A1* 12/2015 Cuevas .................. A61F 2/161
 623/6.16
2020/0397920 A1* 12/2020 Pacal ....................... G02C 7/04

OTHER PUBLICATIONS

Ryosuke Nakaoka et al., "Cytotoxicity of fashionable color contact lenses not aimed at vision correction," Bull.Natl. Inst. Health Sci., Dec. 18, 2007, No. 125, pp. 61-64 (and English machine translation).

* cited by examiner

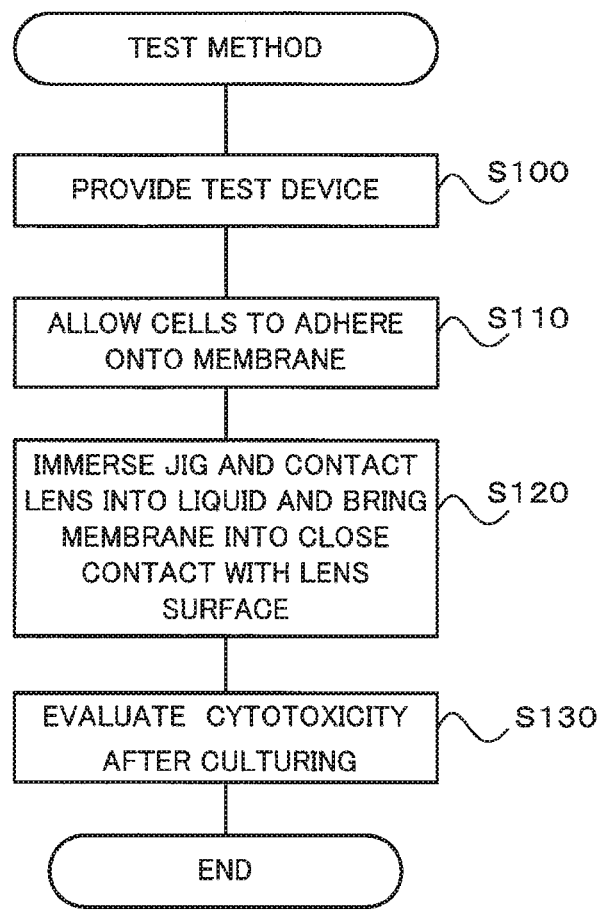

TEST METHOD PERFORMED USING LENS

CROSS REFERENCE TO RELATED APPLICATIONS

The present application claims the priority of Japanese Patent Application No. 2017-250516 filed on Dec. 27, 2017, the entirety of which is incorporated herein by reference.

BACKGROUND

Field

The present disclosure relates to a test method performed using a lens which comes into contact with a human body during use, such as a contact lens.

Related Art

As conventional methods of testing the safety of a contact lens, known are, for example, a method in which cells are cultured in a medium supplemented with an extract of a contact lens and the resulting effects are evaluated; and a method in which a cell culture insert is placed on a contact lens, cells are cultured on a membrane of the cell culture insert, and the resulting effects are evaluated (see, for example, Nonpatent Documents 1 and 2).

Nonpatent document 1: "Safety of fashion color contact lenses with no sight correction purposes (overview)," published on-line on Feb. 3, 2006 by Independent Administrative Agency National Consumer Affairs Center of JAPAN (searched on. Dec. 5, 2017) on the Internet <URL:http://www.kokusen.go.jp/pdf/n-20060203_1.pdf>

Nonpatent document 2: Ryusuke Nakaoka et al., "Cytotoxicity of Various Non-corrective and Decorative Contact Lenses," *Bull.Natl.Inst.Health Sci.*, National Institute of Health Sciences, Dec. 18, 2007, 125, 61-64.

Nonetheless, the method in which an extract of a contact lens is added to a medium is performed under conditions significantly different from those under which a contact lens is worn in contact with the eyeball. This may result in inadequate validity for determining effects of the contact lens. In the method where a membrane of a cell culture insert on which cells are cultured is brought into contact with a lens, the cultured cells may come into contact with the contact lens by way of the membrane, but the contact area is extremely small. Therefore, further improvements in the test methods are required to increase the validity of test results. To enable tests to be performed in various modes, in addition to a method in which a contact lens is brought in contact with cultured cells by way of a membrane, a test method which can be performed with a contact lens coming directly in contact with cultured cells has also been desired. Further, in addition to testing of a contact lens, it has also been desired that an agent (for example, a cleaning liquid, disinfectant liquid, eye drop, or the like for contact lenses) which may be used along with a contact lens, wherein at least a portion of the components thereof may possibly be brought to the eye ball along with a contact lens, can be tested similarly. Furthermore, in addition to contact lenses, an improved test method has similarly been desired for other lenses, such as intraocular lenses, which are brought into contact with a human body when used.

SUMMARY

According to one aspect of the present disclosure, provided is a test method performed using a lens which comes into contact with a human body during use. The above test method comprises: providing a membrane member including a membrane swellable upon absorbing water and a supporting base having an annular shape to support an outer periphery of the membrane; allowing cells to adhere onto the membrane of the membrane member; and bringing the membrane to which the cells are adhered into close contact with a surface of the lens, by immersing the membrane member and the lens into a liquid and deforming the membrane in a swollen state along the surface of the lens.

Advantageous Effects

The test method performed using a lens according to an embodiment of the present disclosure ensures a larger contact area with cells used for the test, leading to an increased sensitive of safety tests performed using a lens as well as increased validity of test results.

BRIEF DESCRIPTION OF THE DRAWINGS

FIG. 1 represents a diagram illustrating a test method performed using a lens;

DETAILED DESCRIPTION

A. First Embodiment

FIG. 1 represents a diagram illustrating a test method according to a first embodiment. The test method shown in FIG. 1 is performed using a lens which comes into contact with a human body during use. More specifically, it is performed while a lens maintains contact with cells. Lenses which comes into contact with a human body during use may include contact lenses and intraocular lenses. Hereinafter, the present disclosure will be described with reference to a case where the lens is a contact lens. However, other types of lenses can be used as well. The test method shown in FIG. 1 can be used to test a lens itself, and can also be used to test an agent (for example, a cleaning liquid, disinfectant liquid, eye drop, or the like for contact lenses) which may be used along with a contact lens, and at least a portion of the components thereof may possibly be brought to the eye ball along with a contact lens. Hereinafter, in the tests performed using contact lenses, tests for evaluating contact lenses and tests for evaluating agents which are to be used along with contact lenses may also be referred to as tests of contact lenses and the like, collectively In a test method according to the present embodiment, a test device 10 is first provided (a step S100). The test device 10 includes as component members a membrane member 20, a lower jig 30, an upper jig 30, and a container portion 50. Hereinafter, the test device 10 used in the present embodiment will be described.

Figure 2A:
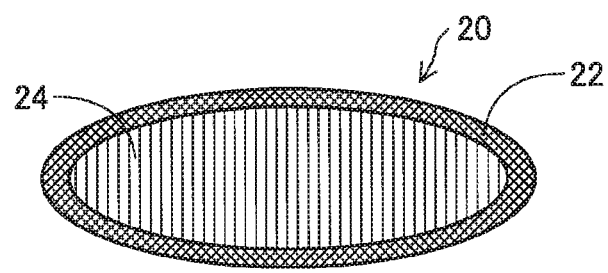
FIG. 2A shows a perspective view of a cell culture ring.
Figure 2B:
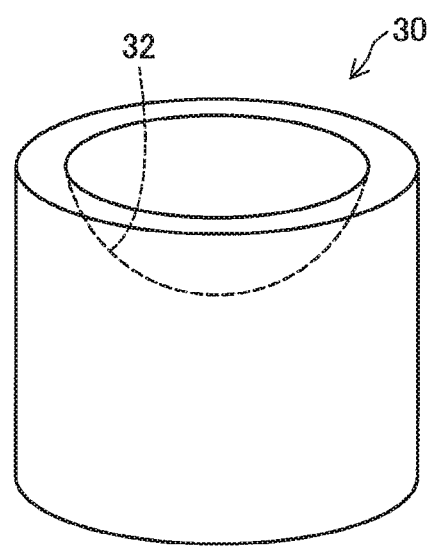
FIG. 2B shows a perspective view of a lower jig.
Figure 3:
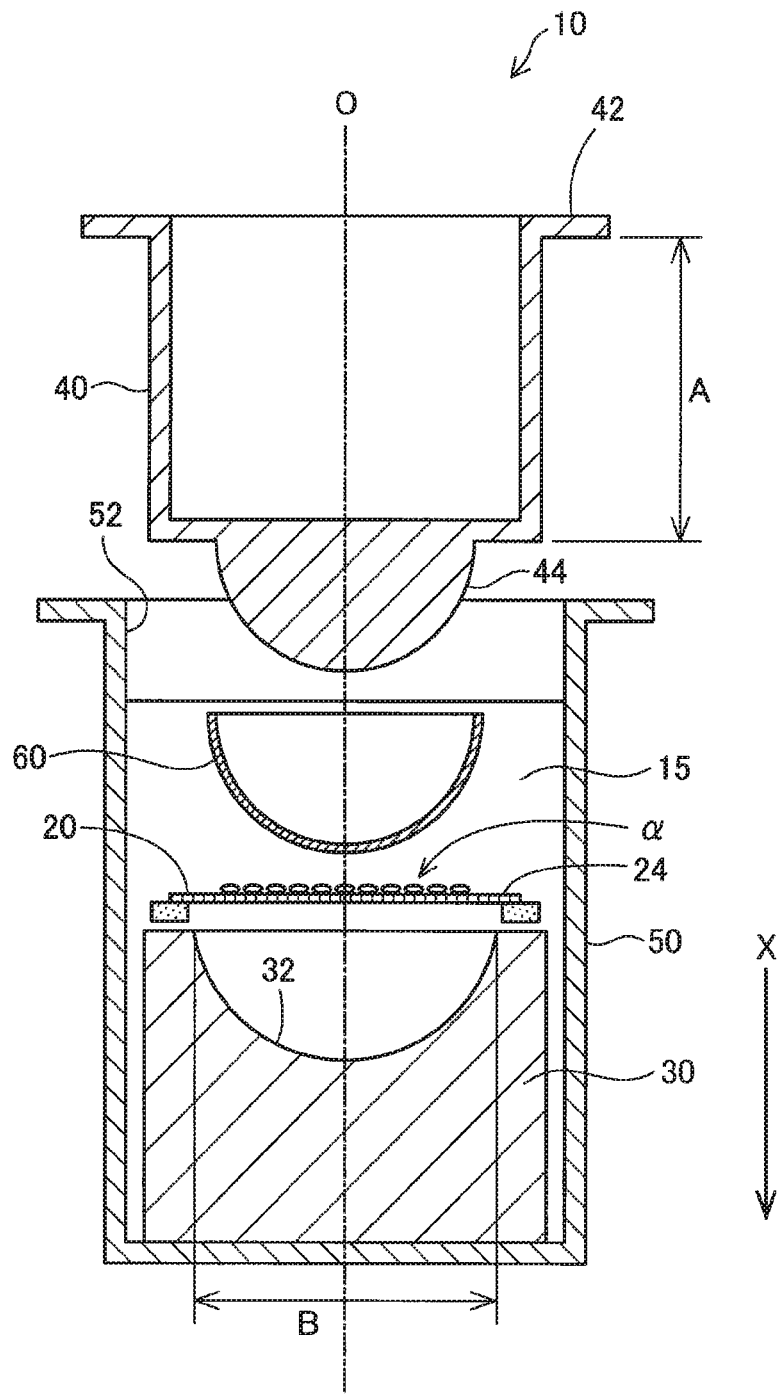
FIG. 3 shows a schematic cross-sectional view of a test device in use for performing a test.

FIG. 2A shows a perspective view of the membrane member 20, and FIG. 2B shows a perspective view of the lower jig 30, and FIG. 20 shows a perspective view of the upper jig 40. FIG. 3 shows a schematic cross-sectional view of the test device 10 in use for testing a contact lens and the like.

The membrane member 20 includes a supporting base 22 and a membrane 24 as shown in FIG. 2A. The supporting base 22 is configured as an annular sheet having a circular hole in the central portion, and is a member configured to hold the membrane 24 in a flat manner. The membrane 24 is configured to have a substantially circular shape, and serves as a scaffold of cultured cells when cell culture is performed. When the outer peripheral portion of the membrane 24 is fixed to the supporting base 22, the entire hole of the supporting base 22 is covered with the membrane 24.

The membrane 24 has a property of absorbing water to swell in a liquid such as a medium. Then, the membrane 24 becomes stretchable as it is softened due to swelling. This enables the membrane 24 to undergo deformation along a curved surface of a contact lens, leading to close contact. The membrane 24 having such characteristics may have a swelling rate of, for example, 1% or more, preferably 3% or more, more preferably 5% or more, and even more preferably 10% or more. The swelling rate as used herein refers to an area swelling rate calculated according to the following formula (1) after immersing the membrane 24 into pure water for 1 hour at room temperature.

Swelling rate (%)=(area after immersion−area before immersion)/area before immersion×100     (1)

The membrane 24 may be formed of a resin selected from, for example, cellulose acetate, cellulose propionate, polyamide 6 copolymer, polyamide 66 copolymer, unsaturated polyester, cellulose nitrate, polyurethane, polyvinyl chloride, acrylic resin, ASA resin, PAS resin, and polyamide 12. In view of the ability of increasing a swelling rate, the membrane 24 is preferably formed of a resin selected from cellulose acetate, cellulose propionate, polyamide 6 copolymer, polyamide 66 copolymer, unsaturated polyester, cellulose nitrate, and polyurethane. These resins have relatively high water absorption rates, and tend to absorb more water to swell more. This enables the swelling rates as described above to be achieved when these resins are formed into a membrane-shaped material.

The membrane 24 may be substantially free from pores, or may be porous. The membrane 24 is preferably porous from the viewpoint that it is suitable for functioning well as a scaffold of cultured cells and a higher swelling rate can be achieved. In a case where the membrane 24 is porous, the average pore size of the pores opening on a side of the membrane to which cultured cells adhere in the membrane 24 may be, for example, 0.1 to 100 μm. Here, the average pore size refers to a value calculated based on observation of a surface of the membrane 24 under a scanning electron microscope (SEM). Specifically, it represents the average value of the largest lengths measured for all of the pores observed in a specific field of a SEM image obtained for the surface of the membrane 24 at 1000× magnification. The above largest length means the largest value of the lengths of the sides of a rectangle circumscribed to a pore. A value of the average pore size falling within the above range can easily establish a desirable balance between the plasticity and strength of the membrane 24. However, the average pore size on a surface of the membrane 24 may be less than 0.1 μm or more than 100 μm. Further, in a case where the membrane 24 is porous, pores formed within the membrane 24 may vary in shape, and may be, for example, through holes formed to pass through the membrane 24 in the membrane thickness direction.

The membrane 24 may have such strength enough for enabling satisfactory handling when a test of a contact lens and the like described below is performed. The dry thickness of the membrane 24 may be, for example, 1 to 100 μm. However, the dry thickness may also be less than 0.1 μm, or more than 100 μm.

The swelling rate of the membrane 24 may vary depending on, in addition to the resin composition of the membrane 24, the membrane thickness of the membrane 24, whether the membrane 24 is porous or not, the shapes of pores and porosity of the membrane 24 if porous, the degree of crystallinity of a resin, and the like. The membrane 24 may swell in a liquid to serve as a scaffold of cultured cells, and may undergo deformation along a curved surface of a contact lens to come into close contact with the lens as described later, and may have such strength enough for enabling satisfactory handling. The membrane 24 is, particularly preferably, a porous polyurethane membrane, because a sufficient swelling rate and strength can be achieved, and a porous membrane which is preferred as a scaffold of cultured cells can be obtained.

A porous polyurethane membrane which is to be used as the membrane 24 can be manufactured as follows, for example. First, an uncured polyurethane raw material is prepared including a polyol such as polyether polyol, an isocyanate such as aromatic isocyanate, and a diluting solvent. Then, a layer of the prepared uncured polyurethane raw material prepared is formed on a substrate. Subsequently; the layer of the uncured polyurethane raw material is cured while steam is supplied to the layer of the uncured polyurethane raw material. Thus, a polyurethane porous membrane can be obtained.

Specifically, methods of supplying steam to the layer of an uncured polyurethane raw material include the followings, for example. The layer of an uncured polyurethane raw material is arranged in a sealed container containing water so that an exposed surface of the layer of the uncured polyurethane raw material on a substrate faces water. Then, the inside of the sealed container is maintained at a predetermined temperature to obtain saturated vapor pressure. This enables steam to be supplied from a surface of the layer of the uncured polyurethane raw material, which in turn allows the isocyanate in the polyurethane raw material to react with the steam, leading to production of carbon dioxide. Meanwhile, a curing reaction is promoted by the polyol and isocyanate. Foaming of the curing polyurethane as described above can produce a porous polyurethane membrane. The shape of a polyurethane porous membrane can be controlled by adjusting conditions selected from the reaction temperature in the aforementioned curing reaction by the supply of steam, the reaction time therein, the amount of steam supplied during curing, and the composition of the polyurethane raw material. That is, the shape and size of each pore, whether the pores are through holes or not, porosity, and the like can be controlled.

The supporting base 22 can be formed of, for example, a resin material or glass. In a case where the supporting base 22 is formed of a resin, the resin may be selected from, for example, polyethylene, polypropylene (PP), silicone resin, polytetrafluoroethylene (PTFE), polyethylene terephthalate (PET), polybutylene terephthalate (PBT), and polymethyl methacrylate (PMMA). The membrane member 20 is preferably formed of a material from which a material possibly affecting the cultured cells (for example, a component such as a metal ion) would not substantially be eluted when cells are seeded and cultured on the membrane 24 or when the tests described later are performed.

In a case where the supporting base 22 is formed of a thermoplastic resin, the membrane 24 can be integrated with the supporting base 22 by, for example, heating a surface of the supporting base 22 which comes in contact with the membrane 24, thereby melting or softening it, and then overlapping and pressing the surface against the membrane 24. Alternatively, the supporting base 22 may be composed of two annular sheets having the same size. In this case, surfaces of the two annular sheets facing each other are respectively heated to be melted or softened, and the membrane 24 is then sandwiched and pressed between the two annular sheets to obtain the membrane member 20. Alternatively, the supporting base 22 may be integrated with the membrane 24 by way of an adhesive.

As shown in FIG. 2B, the lower jig 30 has a substantially cylindrical external shape, and a concave portion 32 having a hemispherically curved surface is formed on a surface of one end portion. The concave portion 32 has a curved surface which follows a convex side of a contact lens 60 as described above.

Figure 2C:
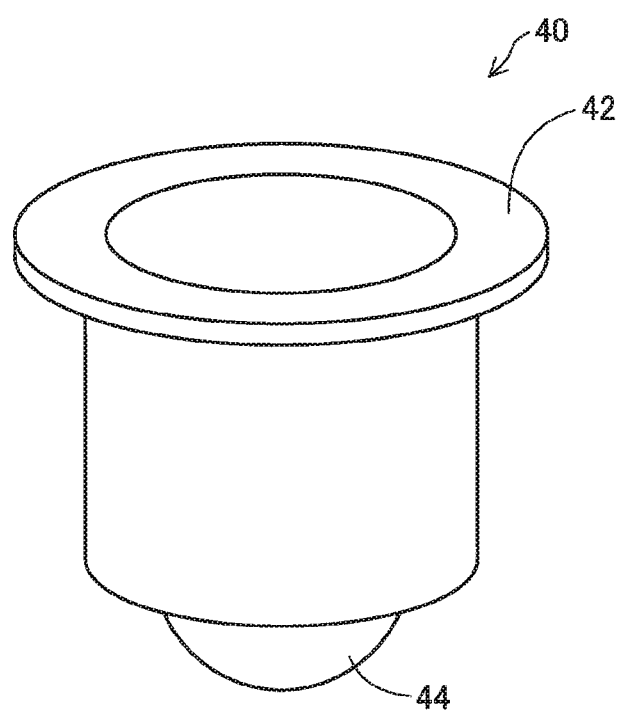
FIG. 2C shows a perspective view of an upper jig.

As shown in FIG. 2C, the upper jig 40 is configured to have a hollow cylindrical shape with one end portion closed. A convex portion 44 having a hemispherically curved surface is formed at the one end portion of the upper jig 40. The convex portion 44 has a curved surface which follows the concave side of the contact lens 60 as described above. The convex portion 44 is intended for supporting the contact lens 60 with the concave side, and may also be referred to as a "supporting portion." Further, a flange 42 overhung outwardly along the circumferential direction is formed at the other end portion, which is open, of the upper jig 40. The upper jig 40 may be configured to have a solid cylindrical shape instead of a hollow cylindrical shape.

The container portion 50, which is a member intended for performing a test of the contact lens 60 and the like therewithin, includes a space (a well 52) having a circular cross-sectional shape which is open toward the upper direction. The membrane member 20, the lower jig 30, and the upper jig 40 are arranged in the well 52 as shown in FIG. 3. In FIG. 3, the alternate long and short dashed line represents the central axis of the test device 10, which is indicated as a central axis O. The central axis O of the test device 10 is in agreement with the central axis of the container portion 50. The central axis O is parallel to the vertical direction, and the vertically downward direction is indicated as the +X direction in FIG. 3.

The diameter of a cross-section (a cross-section perpendicular to the X direction) of the well 52 of the container portion 50 is larger than those of cross-sections of the membrane member 20, the lower jig 30, the upper jig 40, and the contact lens 60. Further, the depth (the length in the X direction) of the well 52 may be such that the membrane member 20 and the contact lens 60 can be immersed into a liquid 15 when the membrane member 20, the lower jig 30, the upper jig 40, and the contact lens 60 are arranged in the well 52. The container portion 50 may be, for example, a plate for cell culture. In this case, each of the wells of the plate for cell culture may serve as the well 52.

The lower jig 30, the upper jig 40, and the container portion 50 can be formed of, for example, a resin material(s) or glass. Resin materials may include a resin selected from, for example, polyethylene, polypropylene (PP), silicone resin, polytetrafluoroethylene (PTFE), polyethylene terephthalate (PET), polybutylene terephthalate (PBT), and polymethyl methacrylate (PMMA). These members are preferably formed of a material(s) from which a material possibly affecting the cultured cells (for example, a component such as a metal ion) would not be substantially eluted.

Returning to FIG. 1, after the test device 10 is provided at the step S100, cells are allowed to adhere onto the membrane 24 of the membrane member 20 (a step S110). Specifically, cells may be seeded on the membrane 24 in a liquid medium, and then be cultured to allow the cultured cells to adhere onto the membrane 24. There is no particular limitation for the cells to be cultured, but cells having similar properties to the cells of the human eyeball are preferred considering that the contact lens 60 that tested is to be worn on the eyeball during use. For example, SIRC (rabbit cornea-derived cells), HCE-T (immortalized human corneal epithelial cells), or human primary cultured corneal epithelial cells can be suitably used. In a culture step after the cells are seeded on the membrane 24, a medium may be appropriately selected depending on the cells used.

For example, when SIRC (rabbit cornea-derived cells) are used as the cells, a 10% FBS-containing E-MEM medium may be used as a medium. Alternatively, for example, when HCE-T is used as the cells, a 10% FBS-containing D-MEM/F12 medium may be used as a medium. Cells may be seeded on the membrane 24 in a medium suitable for the cells, and be cultured to confluency under an environment suitable for the cells (for example, in a $CO_2$ incubator set at 5% $CO_2$ and 37° C. when HCE-T is used as the cells) to allow the cells to adhere onto the membrane 24. It is noted that the membrane 24 is allowed to swell prior to seeding of cells by means of immersion into a medium containing water.

After the cells are allowed to adhere on the membrane 24 in the step S110, the membrane member 20, the lower jig 30, and the upper jig 40 are immersed into the liquid 15 in the well 52 of the container portion 50 along with the contact lens 60 as an evaluation target so that the membrane 24 is brought into close contact with the contact lens 60 (a step S120). In the present embodiment, as shown in FIG. 3, the lower jig 30, the membrane member 20, the contact lens 60, and the upper jig 40 are stacked in this order form the bottom within the well 52 of the container portion 50 containing the liquid 15. At this time, the lower jig 30 is arranged so that the concave portion 32 is oriented upward (in the −X direction), the membrane member 20 is arranged so that a seeding side on which the cells α are seeded is oriented upward, the contact lens 60 is arranged so that the convex side is oriented downward (in the +X direction), and the upper jig 40 is arranged so that the convex portion 44 is oriented downward. Then, the upper jig 40 is pushed down from the state shown in FIG. 3 to press the contact lens 60 with the convex portion 44 of the upper jig 40 from the concave side such that the convex side of the contact lens 60 abuts onto the seeding side of the membrane 24. This enables the back side of the seeding side of the membrane 24 to abut onto the concave portion 32 of the lower jig 30. When each member is stacked as shown in FIG. 3, for example, the contact lens 60 swollen with water can be temporarily attached on a surface of the convex portion 44. This can allow an operation of stacking the respective members to be performed while the contact lens 60 is temporarily fixed to the convex portion 44 as described above.

The membrane 24 of the present embodiment, which has acquired stretchability after being swollen and softened as described above, can undergo deformation along the convex side of the contact lens 60 to achieve close contact therewith when pressed against the convex side of the contact lens 60. The membrane 24 preferably covers and forms close contact with, for example, 80% or more of a surface of the contact lens 60, more preferably 90% or more, and even more preferably 95% or more. The membrane 24 can be more easily brought into close contact with a larger region of a surface of the contact lens 60 as the swelling rate of the membrane 24 increases. The membrane 24 can be brought into close contact with the entirety of the surface of the contact lens 60 by selecting a membrane 24 having an appropriate swelling rate and a size large enough for the convex side of the contact lens 60.

Figure 4:
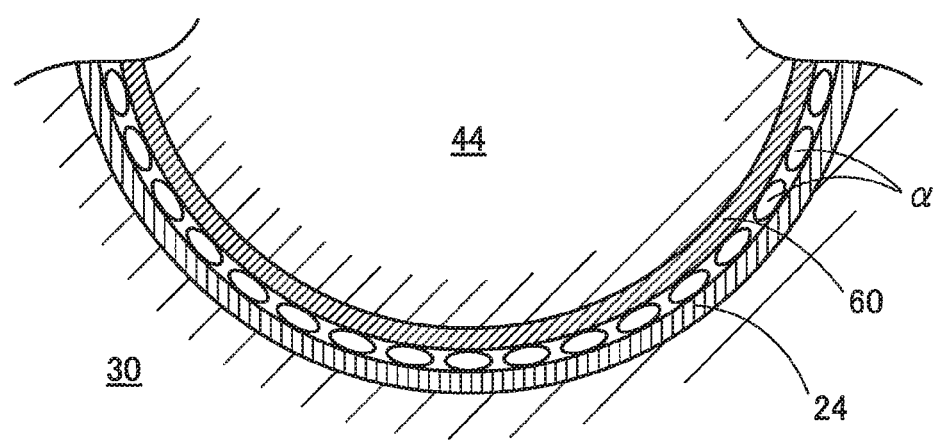
FIG. 4 shows a schematic cross-sectional view of a state where cells are in contact with a lens.

FIG. 4 shows a schematic cross-sectional view of a test device in which, by pressing down the upper jig 40 as described above, the convex side of the convex portion 44, the contact lens 60, and the membrane 24 having the cells α are stacked on the lower jig 30, such that the cells α are brought into contact with the contact lens 60 in the step S120. The surface of the concave portion 32 of the lower jig 30 has a curvature which is substantially same as that of the convex side of the contact lens 60, and is shaped to allow for exact mutual fitting. Further, the concave side of the contact lens 60 has a curvature which is substantially the same as that of the surface of the convex portion 44 of the upper jig 40, and is shaped to allow for exact mutual fitting. Here, a pressing force experienced by the cells α sandwiched between the lower jig 30 and the contact lens 60 is preferably adjusted so that effects on the viability or proliferation of the cells α caused by the pressing force experienced by the cells α fall within an acceptable range. In the present embodiment, the pressing force applied to the cells α when the flange 42 of the upper jig 40 is engaged with the upper end portion of the container portion 50 can be controlled to fall within an acceptable range by adjusting the distance (indicated as a distance A in FIG. 3) from the flange 42 of the upper jig 40 to the convex portion 44. Further, in the present embodiment, the entirety of the contact lens 60 brought into contact with the cells a can be supported from underneath with the lower jig 30 by making the diameter (indicated as a distance B in FIG. 3) of the concave portion 32 sufficiently large (for example, about 2 mm larger than the diameter of the contact lens 60).

In FIG. 3, the liquid 15 may be, for example, a liquid medium suitable for culturing the cells α used. If the cells α are cultured for a relatively short time after the step S120, the liquid 15 may also be a liquid having a simpler composition than a medium usually selected for the cells α (for example, a liquid having less components, but a large water content). The liquid 15 preferably contains at least a part of the components of the medium for cell culture. This enables tests to be performed using a contact lens while maintaining cultured cells in better conditions. The liquid 15 preferably contains at least L-glutamine as an component of the medium for cell culture.

Further, after performing an operation of stacking each member of the test device 10 with the contact lens 60, a liquid in the well 52 may be replaced with the liquid 15 suitable for a test purpose in the step S120.

Further, in order to test the effects of an agent or the like which is to be used along with a contact lens (for example, a cleaning liquid, disinfectant liquid, eye drop, or the like for contact lenses) using the test device 10, that agent may be added to the liquid 15. Specifically, for example, a plurality of test devices 10 may be provided, and equal volumes of an agent with different dilution factors may be added to the liquid 15 in each of the test devices 10. The effects of the agent can be then studied by culturing the cells α in a test liquid including the liquid 15 and the agent while the membrane 24 maintains close contact with the contact lens 60.

After the step S120, the cells α are cultured as needed while the cells α maintain close contact with the contact lens 60, and cytotoxicity is then evaluated (a step S130). When testing the contact lens 60, a lens known in advance to have no toxicity and having the same shape (the same curvature, same thickness, and same diameter) as that of the contact lens 60 which is the evaluation target may be used as a negative control. Further, a lens known in advance to have toxicity and having the same shape as that of the contact lens 60 which is the evaluation target may be used as a positive control. There is no particular limitation for the methods of evaluating cytotoxicity, but examples thereof may include a method in which the viability of cells after culture (a ratio of the number of survived cells to the number of cells before culture) or the growth ratio (a ratio of the number of cells increased after culture to the number of cells before culture) thereof is determined. After the cells a are sandwiched between the contact lens 60 and the lower jig 30 and cultured, the number of the viable cells α may be determined, for example, by a method in which enzyme activity using various types of tetrazolium salts such as MTT and WST (Water soluble Tetrazolium salts) is measured colorimetrically.

According to the test method of the present embodiment designed as described above, a larger contact area of the contact lens 60 with the cells α used for the test can be ensured. This can increase the sensitivity of a safety test performed using a contact lens, and can also increase the validity of test results. Moreover, according to the present embodiment, the test can be performed in a state where the contact lens 60 is in direct contact with the cells α. This means that the contact lens 60 can be tested under conditions closer to those under which the contact lens 60 would be used on a human body.

Further, in the test device 10 according to the present embodiment, the contact lens 60 is pressed against the membrane 24 on which the cells α are adhered to while being supported from the concave side by the upper jig 40 (the convex portion 44) having a shape coincident with the curved surface of the contact lens 60. Therefore, the deformation of the contact lens 60 can be prevented when the contact lens 60 is pressed against the membrane 24. As a result, the adhesion of the contact lens 60 with the membrane 24 can be further improved. According to the test method of the present embodiment, a test can be similarly performed regardless of whether the contact lens 60 is a soft contact lens or a hard contact lens. In a case where a soft contact lens is used, the deformation of the contact lens 60 can be prevented by using the above configuration, leading to particularly significant effects for increasing the adhesion with the membrane 24.

Figure 13:
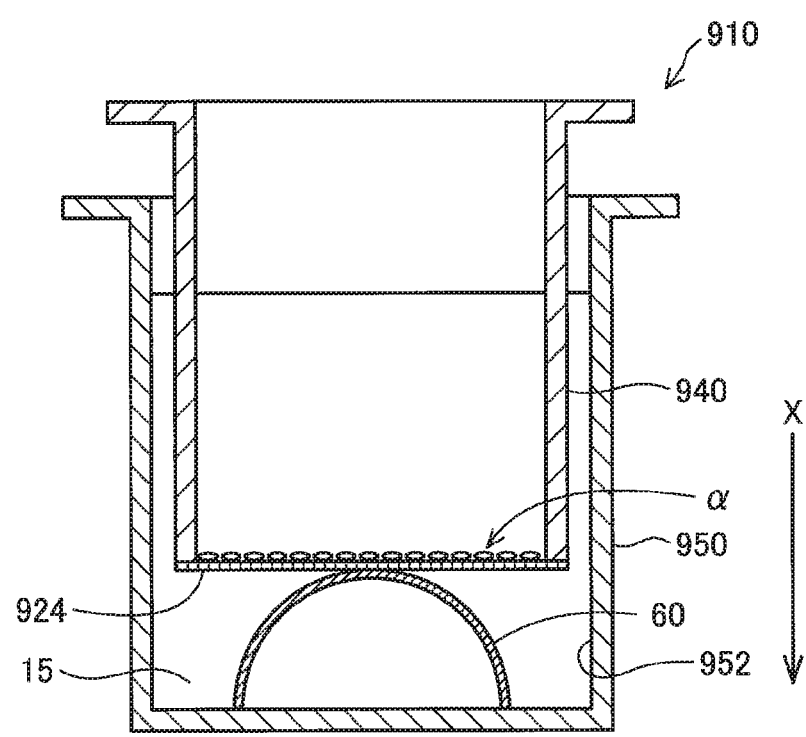
FIG. 13 shows a schematic cross-sectional view of a test device for illustrating a conventionally known test method.

FIG. 13 shows a schematic cross-sectional view of a test device for illustrating a method of testing the toxicity of a contact lens using a cell culture insert as a comparative example. In a test device 910 shown in FIG. 13, the contact lens 60 is arranged in a well 952 of a plate 950 for cell culture, and a cell culture insert 940 is arranged on the contact lens 60. The cell culture insert 940 includes a membrane 924 having through holes so that the membrane 924 covers the entire opening at the lower end of a tubular housing. The cell culture insert 940 as described above is generally used in experiments performed with cultured cells in which the cells α are seeded on a surface of the membrane 924 exposed in the housing.

A membrane provided in a conventionally known cell culture insert generally includes polycarbonate (PC) or polyethylene terephthalate (PET). A resin such as PC and PET, which has a smaller water absorption rate as compared with the resins mentioned above as those preferred for the membrane 24 used in the present embodiment, may undergo almost no swelling in a liquid even though it has through holes, which means that neither softening due to swelling nor acquisition of stretchability tends to occur. Therefore, even when the cell culture insert 940 is pressed from above against the contact lens 60 in the liquid 15 within the well 952, the membrane 924 is brought into contact with only a limited region of the apex portion of the contact lens 60. That is, a membrane 824 on which the cells α are adhered to cannot be brought into close contact with the surface of the contact lens 60 by forcing the membrane to deform along the surface of the contact lens 60 as in the present embodiment.

When the cell culture insert 940 is pressed more strongly against the contact lens 60 to increase the contact area with the contact lens 60 in FIG. 13, if the contact lens 60 is relatively soft, the contact lens 60 may become deformed and flattened, resulting in inability to come in close contact with the membrane 924. Further, if the contact lens 60 is relatively hard, the membrane 924 may be damaged when the cell culture insert 940 is pressed more strongly against the contact lens 60. In both cases, if the membrane 924 in which softening and stretching due to swelling is less likely to occur is used, the membrane 924 can only cover and form close contact with less than 80% of the surface of the contact lens 60. Moreover, according to the method shown in FIG. 13, unlike the present embodiment, tests cannot be performed while bringing the cells α in direct contact with the contact lens 60.

Described hereinafter are results from studies of the swelling rates of the membrane 24 of the present embodiment and of the membrane 924 provided in the cell culture insert 940 which is conventionally known. As the membrane 24 of the present embodiment, used was a polyurethane porous membrane (hereinafter, also referred to as a PU membrane) produced by curing a layer of an uncured polyurethane raw material formed on a substrate while supplying steam to the layer of the polyurethane raw material as described above. In the following description, a side exposed on the substrate during manufacture of the PU membrane is called a front side, and a side in contact with the substrate is called a back side. As the membrane 924 of the cell culture insert 940, used was a Costar® Transwell insert (Corning, Inc.), 24-well, membrane diameter: 6.5 mm, membrane pore size: 8.0 μm (hereinafter, also referred to as an IS membrane). The IS membrane provided in the cell culture insert 940 is made of polycarbonate.

For each of the PU membrane and the IS membrane, the average dry pore size, the dry porosity, the dry membrane thickness, and the swelling rate were studied. As for the average pore size, a surface of each membrane was observed under a scanning electron microscope (SEM) to measure the largest length of each of the pores observed in a given field of a SEM image, and the average value was calculated from the measured values. The largest length herein refers to the largest value of the lengths of the sides of a rectangle circumscribed to a pore. The porosity refers to a proportion of the total area of all pores observed on a surface of each membrane in a 2000× field under a laser microscope relative to the area of the entire field. The swelling rate is an area swelling rate computed by the formula (1) described above after each membrane is immersed into pure water for 1 hour at room temperature.

As for the PU membrane of the present embodiment, the average pore size was 8.5 μm and the porosity was 61% at the front side, while the average pore size was 7.0 μm and the porosity was 15% at the back side. Further, the PU membrane had a membrane thickness of 6.5 μm and a swelling rate of 10.5% (the dry area was 113.1 mm$^2$, and the area after being immersed in pure water was 125.0 mm$^2$).

The IS membrane had an average pore size of 7.7 μm and a porosity of 15% at the both sides. Further, the IS membrane had a membrane thickness of 14.5 μm and a swelling rate of −5.6% (the dry area was 38.0 mm$^2$, and the area after being immersed in pure water was 36.0 mm$^2$).

The IS membrane provided in a cell culture insert conventionally used for a test in which cells are in contact with a contact lens cannot, even when pressed against while on the contact lens, undergo deformation along a surface of the contact lens to be brought into close contact with the surface of the contact lens. Such an IS membrane was found to show no swelling after being immersed into pure water as described above.

Hereinafter, examples will be described in which the test device 10 was found to be capable of bringing the membrane 24 of the present embodiment into close contact with the entirety of the surface of the contact lens 60. Here, used as the membrane 24 was a membrane having a diameter of 12 mm which was similar to the PU membrane used for measuring the expansion rate above. Then the entirety of one surface of the membrane 24 having no cells was coated with a lycopene solution. Then, the coated surface and a convex side of the contact lens 60 were arranged so as to face each other, and the coated surface was brought into contact with the contact lens 60 by way of the test device 10 of FIG. 3. After holding such a contacting state for 5 seconds, the contact lens 60 was removed from the test device 10, and the surface of the contact lens 60 was observed. Results showed that the surface of the contact lens 60 was entirely stained with lycopene. This demonstrated that the test device 10 was able to bring the membrane 24 into close contact with the entirety of the surface of the contact lens 60.

B. Second Embodiment

A device different from the test device 10 shown in FIG. 3 may be used when a membrane to which cells are adhered is brought into close contact with a surface of a contact lens by allowing the membrane in a swollen state to undergo deformation along the surface of the contact lens. The test device may include a lower jig and an upper jig each including a convex portion or a concave portion each having a shape mutually corresponding with a curved surface of the contact lens. Further, the test device may include a membrane member including a membrane swellable upon absorbing water and a supporting base configured to have an annular shape to support an outer periphery of the membrane. Cells may be allowed to adhere on the membrane of the membrane member, and that membrane may be then arranged between the contact lens and the lower jig or between the contact lens and the upper jig. Hereinafter, various embodiments of the test device will be described.

Figure 5:
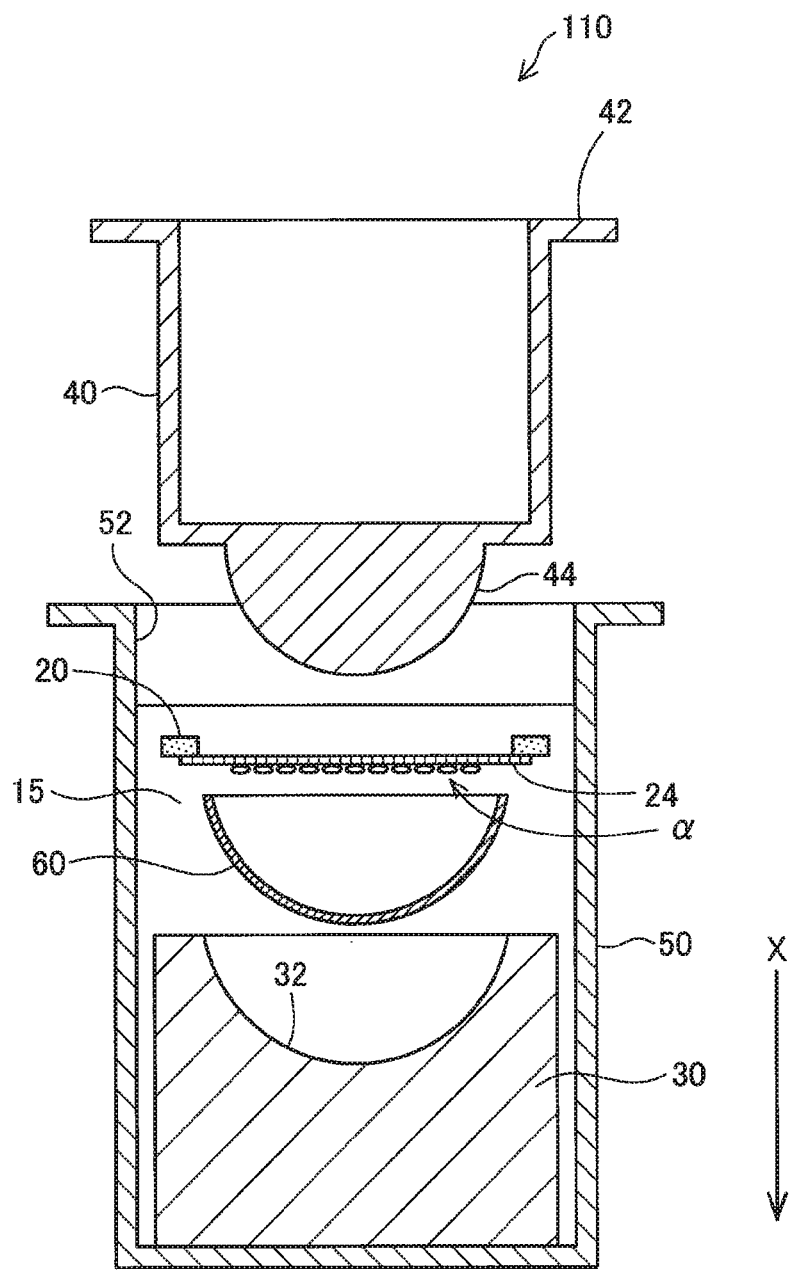
FIG. 5 shows a schematic cross-sectional view of a test device in use for performing a test.

FIG. 5 shows, similarly to FIG. 3, a cross-sectional view of the configuration of a test device 110 to be used in the method of testing a contact lens and the like according to a second embodiment. In the second embodiment, the same reference numerals are assigned to parts common with the first embodiment, and detailed descriptions thereof are omitted.

The test device 110 according to the second embodiment differs from the test device 10 according to the first embodiment in that the membrane member 20 is arranged between the contact lens 60 and the upper jig 40 instead of between the contact lens 60 and the lower jig 30. Also, in the test device 110, the membrane member 20 is arranged upside down as compared with the first embodiment, and a side of the membrane 24 having the cells α is brought into contact with a concave side of the contact lens 60 by pushing the membrane 24 with the convex portion 44 of the upper jig 40.

This configuration can also produce similar effects as the first embodiment. In particular, in the second embodiment, the cells α can be brought into contact with the concave side of the contact lens 60, which means that the contact lens 60 can be tested under conditions closer to those under which the contact lens 60 would be used in a human body.

C. Third Embodiment

Figure 6:
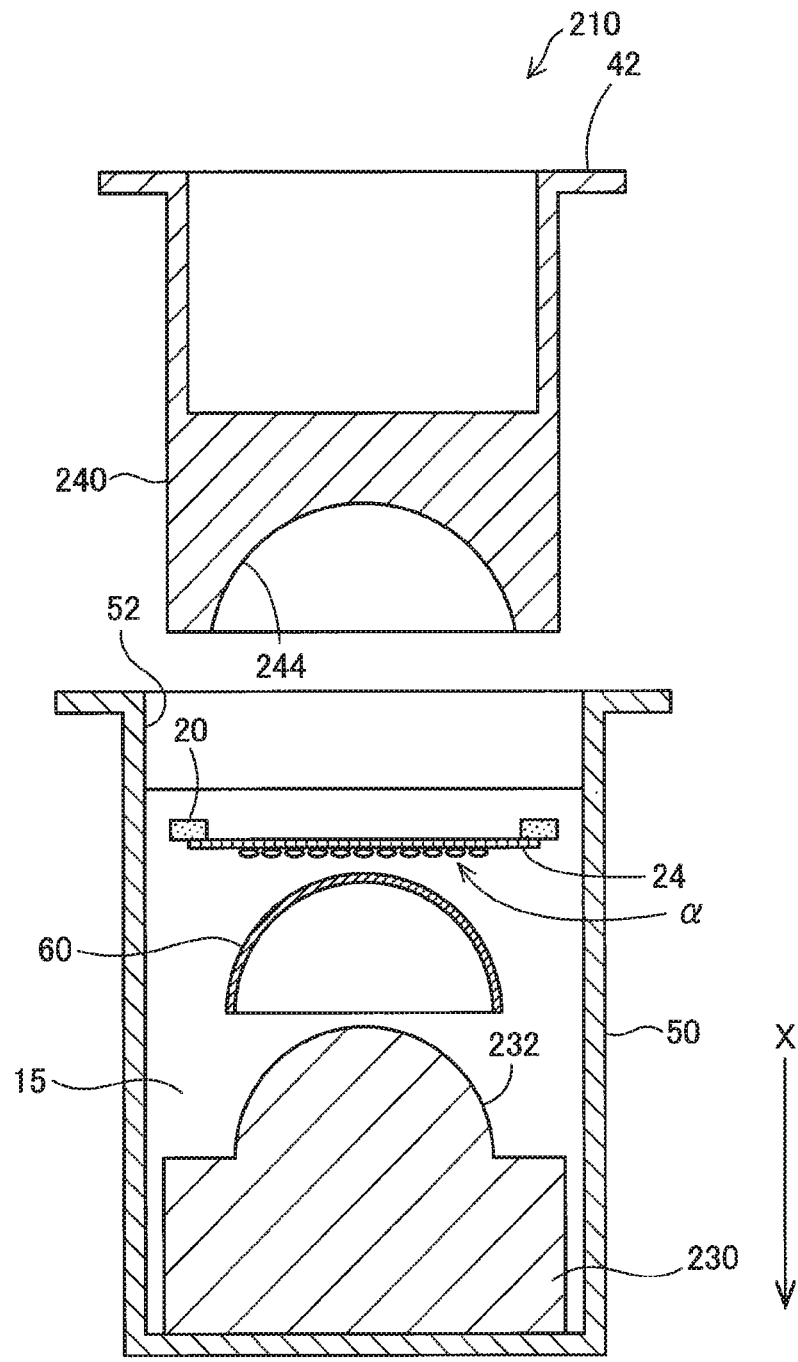
FIG. 6 shows a schematic cross-sectional view of a test device in use for performing a test.

FIG. 6 shows, similarly to FIG. 3, a cross-sectional view of the configuration of a test device 210 to be used in the method of testing a contact lens and the like according to a third embodiment. In the third embodiment, the same reference numerals are assigned to parts common with the first embodiment, and detailed descriptions thereof are omitted.

The test device 210 according to the third embodiment includes a lower jig 230 having a convex portion 232 instead of the lower jig 30 having the concave portion 32, and upper jig 240 having a concave portion 244 instead of the upper jig 40 having the convex portion 44. Here, the convex portion 232 and the concave portion 244 are respectively configured to have a shape mutually corresponding with a curved surface of the contact lens. Further, the contact lens 60 is arranged on the lower jig 230 so that the convex side is oriented vertically upward. (in the −X direction). The convex portion 232 is a region intended for supporting the contact lens 60 with the concave side, and may also be referred to as a "supporting portion." Further, the membrane member 20 is arranged between the contact lens 60 and the upper jig 240 while a side on which the cells α are adhered to is facing the contact lens 60, and is used with the side of the membrane 24 on which the cells α are adhered to maintaining contact with a convex side of the contact lens 60. This configuration can also produce similar effects as the first embodiment.

D. Fourth Embodiment

Figure 7:
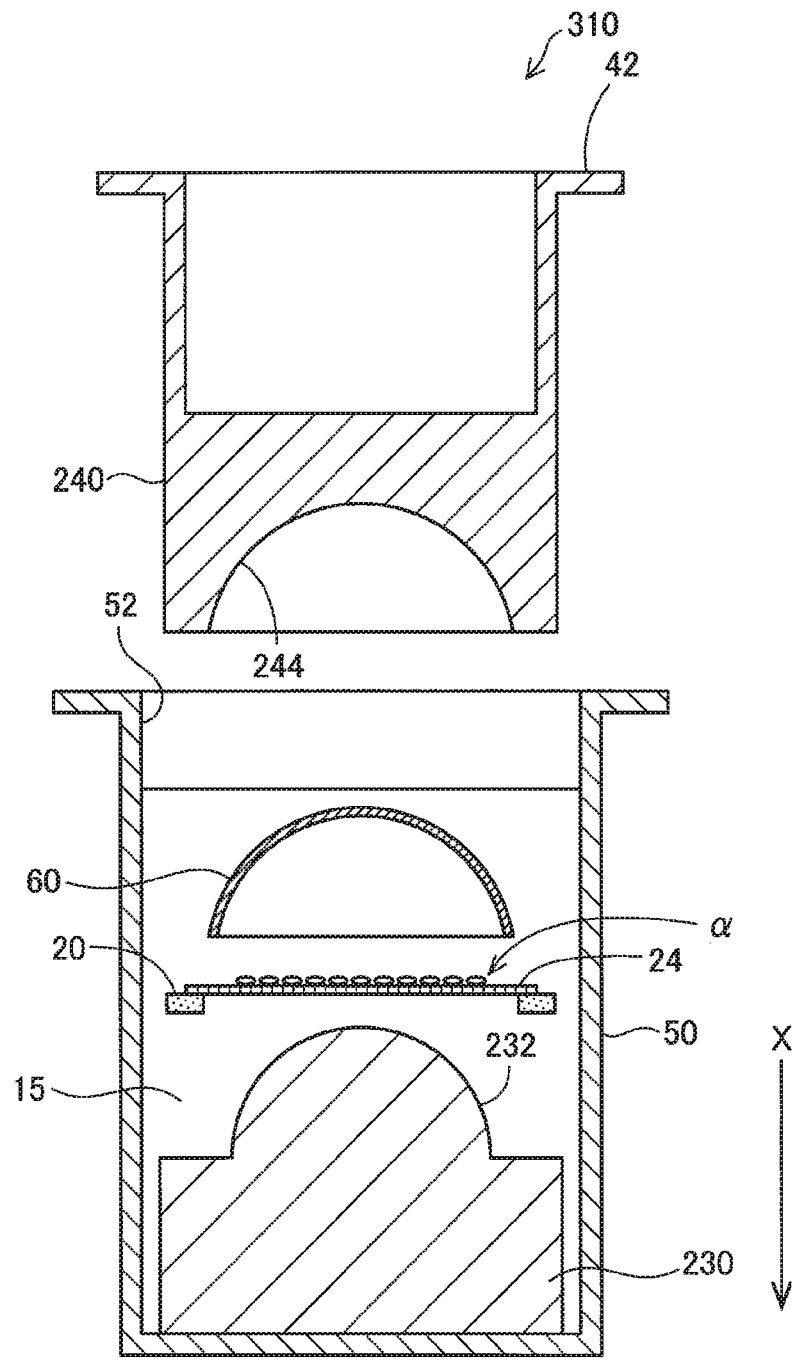
FIG. 7 shows a schematic cross-sectional view of a test device in use for performing a test.

FIG. 7 shows, similarly to FIG. 3, a cross-sectional view of the configuration of a test device 310 which is to be used in the method of testing a contact lens and the like according to a fourth embodiment. In the fourth embodiment, the same reference numerals are assigned to parts common with the third embodiment, and detailed descriptions thereof are omitted.

The test device 310 according to the fourth embodiment differs from the test device 210 according to the third embodiment in that the membrane member 20 is arranged between the contact lens 60 and the lower jig 230 instead of between the contact lens 60 and the upper jig 240. In the test device 310, the membrane member 20 is arranged upside down as compared with the third embodiment, and a side of the membrane 24 having the cells α is brought into contact with a concave side of the contact lens 60 by supporting the membrane 24 and the contact lens 60 from underneath with the convex portion 232 of the lower jig 230.

This configuration can also produce similar effects as the third embodiment. In particular, in the fourth embodiment, the cells α can be brought into contact with the concave side of the contact lens 60, which means that the contact lens 60 can be tested under conditions closer to those under which the contact lens 60 would be used in a human body.

E. Fifth Embodiment

Figure 8:
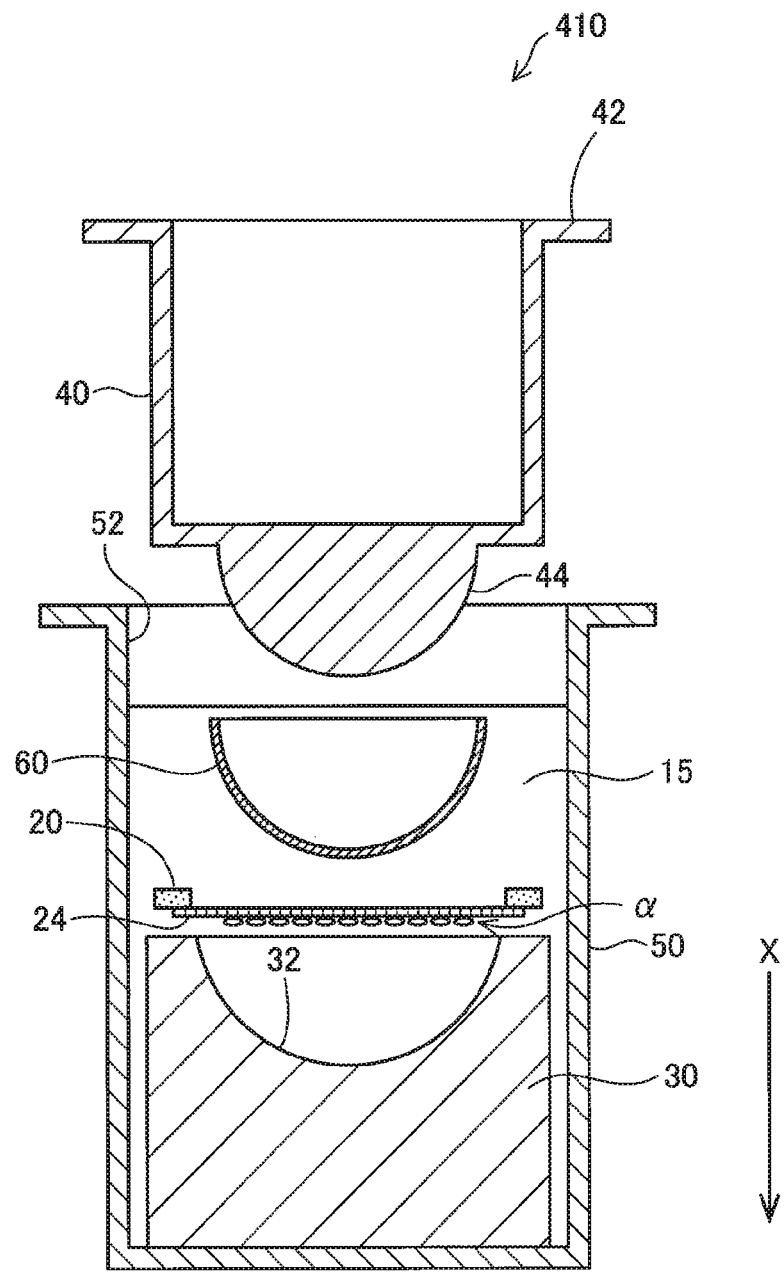
FIG. 8 shows a schematic cross-sectional view of a test device in use for performing a test.

FIG. 8 shows, similarly to FIG. 3, a cross-sectional view of the configuration of a test device 410 which is to be used in the method of testing a contact lens and the like according to a fifth embodiment. In the fifth embodiment, the same reference numerals are assigned to parts common with the first embodiment, and detailed descriptions thereof are omitted.

The test device 410 according to the fifth embodiment differs from the test device 10 according to the first embodiment in that the membrane member 20 is arranged upside down. The membrane 24 according to the fifth embodiment also differs from the membrane 24 according to the first embodiment in that pores of the membrane 24 in the first embodiment may be open only on the side which is to be in contact with the cells α or may be through holes formed to pass through the membrane 24 in the membrane thickness direction, while the membrane 24 according to the fifth embodiment has through holes.

This configuration can also produce similar effects as the first embodiment. In the fifth embodiment, unlike in the first embodiment, the cells α on the membrane 24 is brought into contact with the surface of the contact lens 60 via the through holes of the membrane 24.

F. Sixth Embodiment

Figure 9:
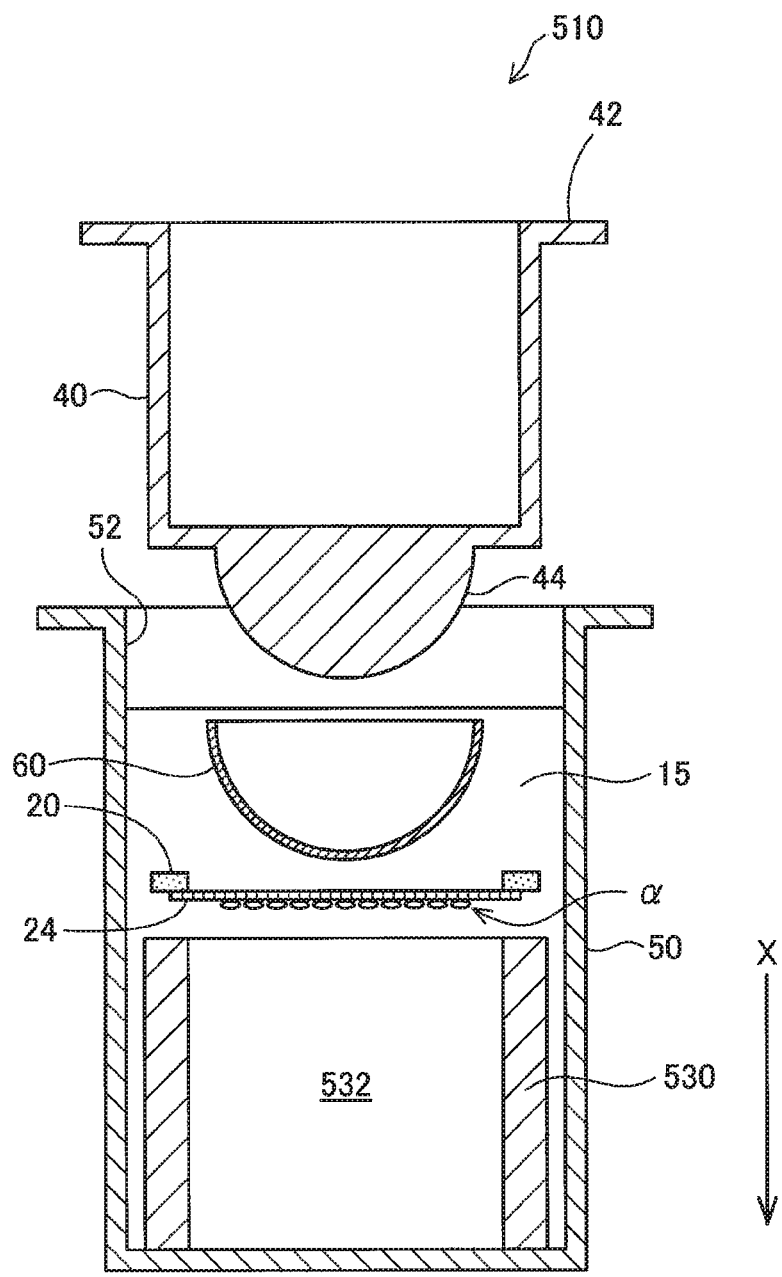
FIG. 9 shows a schematic cross-sectional view of a test device in use for performing a test.

FIG. 9 shows, similarly to FIG. 8, a cross-sectional view of the configuration of a test device 510 which is to be used in the method of testing a contact lens and the like according to a sixth embodiment. In the sixth embodiment, the same reference numerals are assigned to parts common with the fifth embodiment, and detailed descriptions thereof are omitted.

The test device 510 according to the sixth embodiment differs from the test device 410 according to the fifth embodiment in that a lower jig 530 is used instead of the lower jig 30. The lower jig 530 is configured to have a hollow cylindrical shape having an opening at an end portion in the vertically upward direction (in the −X direction). When the upper jig 40 is pushed down in the vertically downward direction (in the +X direction), the convex portion 44 of the upper jig 40, the contact lens 60 supported from the concave side by the convex portion 44, and the membrane 24 pressed by the contact lens 60 to undergo deformation along the convex side of the contact lens 60 are housed in a space 532 inside the lower jig 530 through the opening.

This configuration can also produce similar effects as the fifth embodiment. Particularly, in the sixth embodiment, the cells α are exposed in the space 532 of the member (the lower jig 530) adjacent to the membrane member 20 without being in contact with the adjacent lower jig 530. This configuration can reduce influence resulting from the pressure applied to the cells α when a test is performed.

G. Seventh Embodiment

Figure 10:
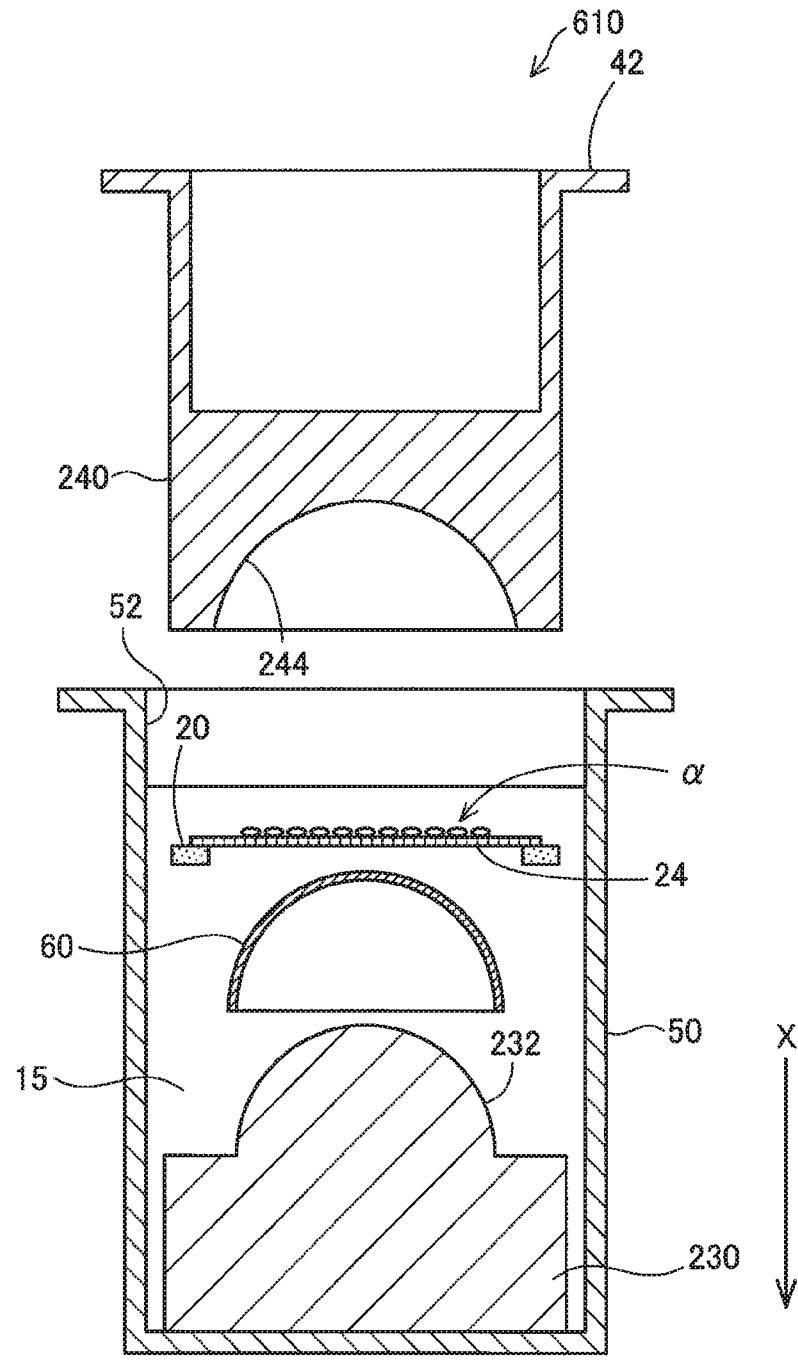
FIG. 10 shows a schematic cross-sectional view of a test device in use for performing a test.

FIG. 10 shows, similarly to FIG. 6, a cross-sectional view of the configuration of a test device 610 which is to be used in the method of testing a contact lens and the like according to a seventh embodiment. In the seventh embodiment, the same reference numerals are assigned to parts common with the third embodiment, and detailed descriptions thereof are omitted.

The test device 610 according to the seventh embodiment differs from the test device 210 according to the third embodiment in that the membrane member 20 is arranged upside down. The membrane 24 in the seventh embodiment differs from the membrane 24 in the third embodiment in that pores of the membrane 24 according to the third embodiment may be open only on the side to be in contact with the cells α or may be through holes formed to pass through the membrane 24 in the membrane thickness direction, while the membrane 24 according to the seventh embodiment has through holes.

This configuration can also produce similar effects as the third embodiment. In the seventh embodiment, unlike in the third embodiment, the cells a on the membrane 24 is brought into contact with the surface of the contact lens 60 via the through holes of the membrane 24.

H. Eighth Embodiment

Figure 11:
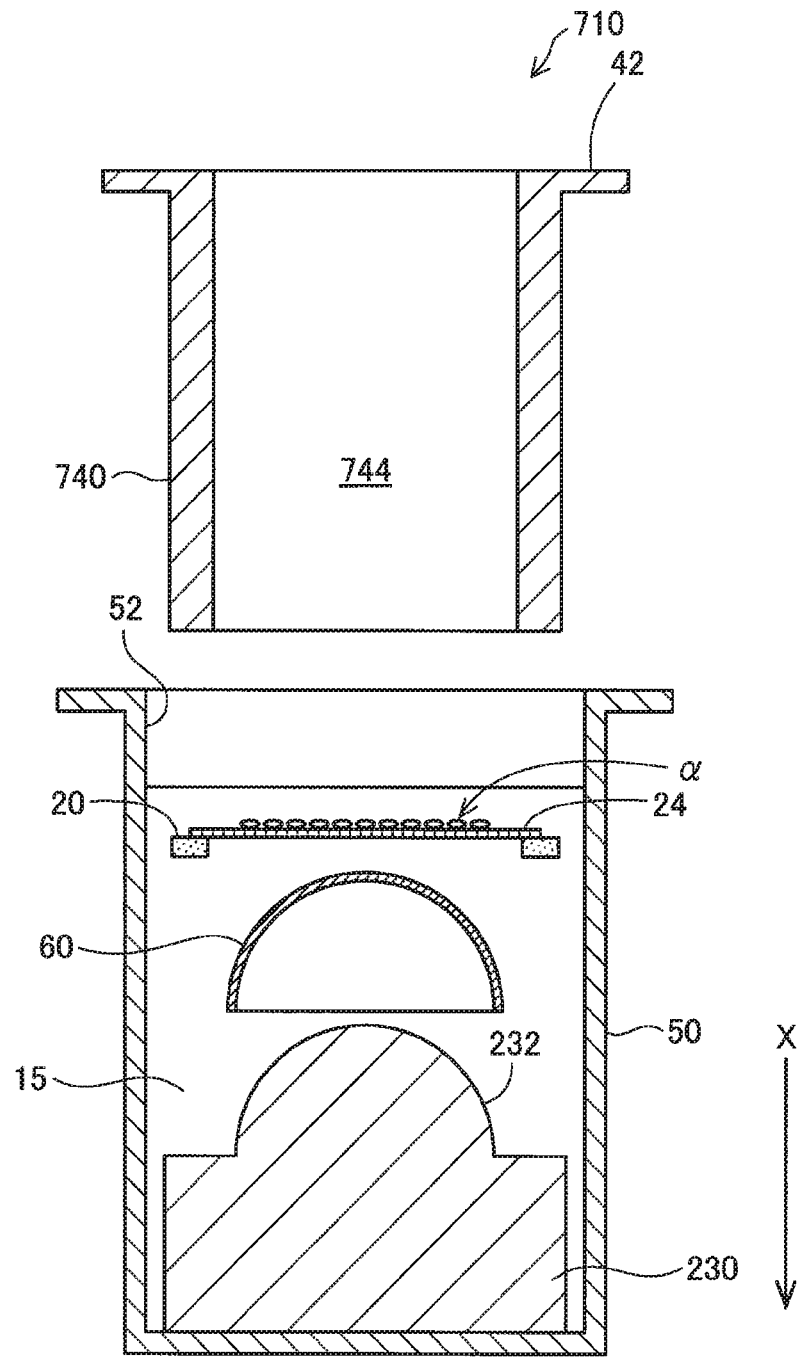
FIG. 11 shows a schematic cross-sectional view of a test device in use for performing a test.

FIG. 11 shows, similarly to FIG. 10, a cross-sectional view of the configuration of a test device 710 which is to be used in the method of testing a contact lens and the like according to an eighth embodiment. In the eighth embodiment, the same reference minerals are assigned to parts common with the seventh embodiment, and detailed descriptions thereof are omitted.

The test device 710 according to the eighth embodiment differs from the test device 610 according to the seventh embodiment in that an upper jig 740 is used instead of the upper jig 240. The upper jig 740 is configured to have a substantially hollow cylindrical shape having an opening at the end portion in the vertically downward direction (the +X direction). When the upper jig 740 is pushed down in the vertically downward direction (in the +X direction), the convex portion 232 of the lower jig 230, the contact lens 60 supported from the concave side by the convex portion 232, and the membrane 24 pressed by the contact lens 60 to undergo deformation along the convex side of the contact lens 60 are housed in a space 744 inside the upper jig 740 through the opening.

This configuration can also produce similar effects as the seventh embodiment. Particularly, in the eighth embodiment, the cells α are exposed in the space 744 of the member (the upper jig 740) adjacent to the membrane member 20 without being in contact with the adjacent upper jig 740. This configuration can reduce influence resulting from pressure applied to the cells α when a test is performed.

I. Ninth Embodiment

In the first to eighth embodiments, test devices are used each including a lower jig and an upper jig having a convex portion or a concave portion each having a shape mutually corresponding with a curved surface of the contact lens. However, a test device having a different configuration may be used to bring a membrane to which cells are adhered into close contact with a surface of a contact lens. Hereinafter, an example of such a configuration will be described as a ninth embodiment.

Figure 12A:
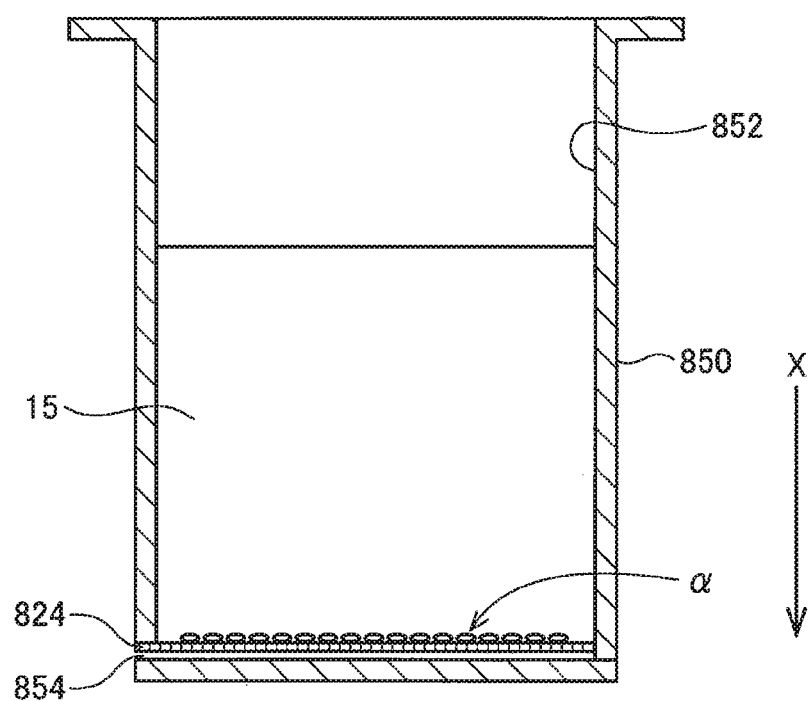
FIG. 12A shows a cross-sectional view of a test device for illustrating a test method performed using a lens.
Figure 12B:
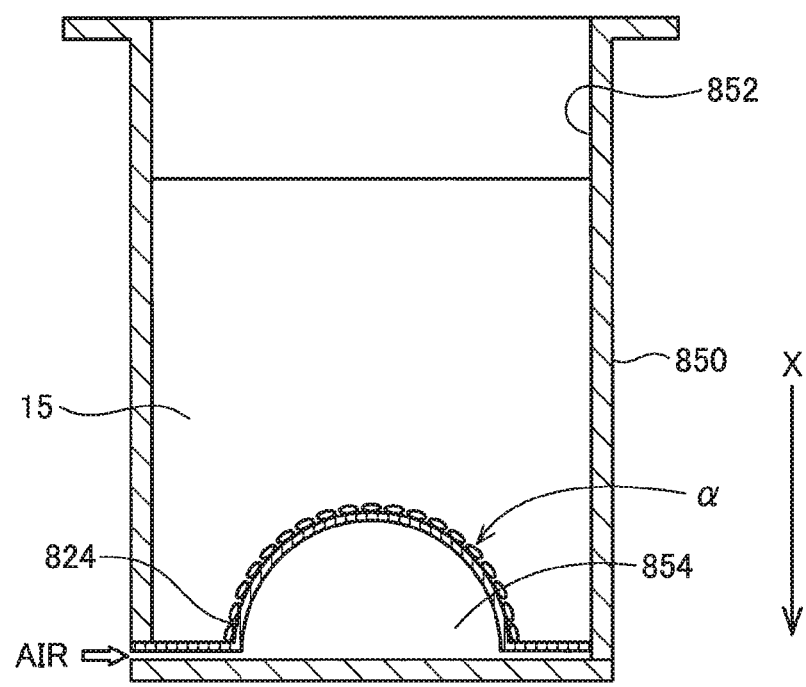
FIG. 12B shows a cross-sectional view of a test device for illustrating a test method performed using a lens.
Figure 12C:
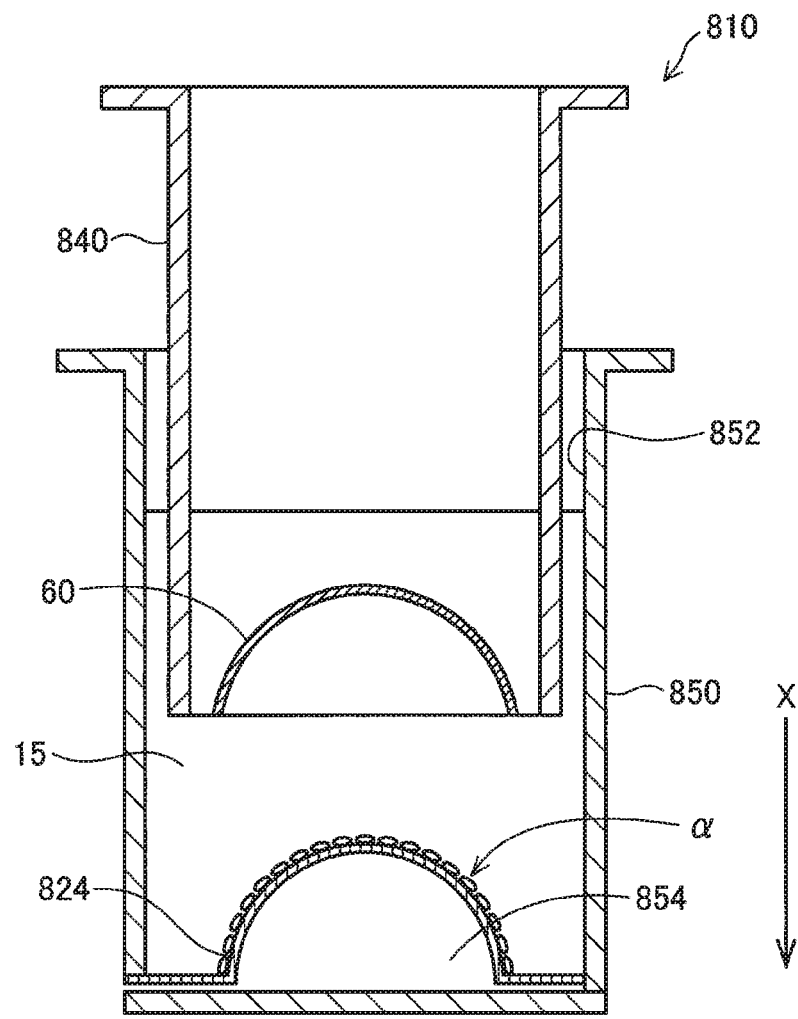
FIG. 12C shows a cross-sectional view of a test device for illustrating a test method performed using a lens.

FIGS. 12A to 12C show a cross-sectional view of a test device for illustrating a method of testing a contact lens and the like according to the ninth embodiment. In the ninth embodiment, a test device 810 is used. The same reference numerals are assigned to parts common with the first embodiment, and detailed descriptions thereof are omitted.

The test device 810 according to the ninth embodiment includes, as shown in FIG. 12C, a container portion 850 and an upper jig 840. The container portion 850 includes a space (a well 852) having a circular cross-sectional shape and having an opening at the top. As shown in FIG. 12C, the upper jig 840 is arranged within the well 852 when the contact lens 60 or the like is tested. As shown in FIG. 12A, a membrane 824 is arranged at the bottom of the well 852 of the container portion 850 so as to cover the bottom of the well 852. The membranes 824 is similar to the membranes 24 used in the first to eighth embodiments. According to the ninth embodiment, the container portion 850 may also be referred to as a supporting base in the sense that the end portion of the container portion 850 in the vertically downward direction supports the outer periphery of the membrane 824. The container portion 850 and the membrane 824 may also be referred to a membrane member, collectively. In the container portion 850, a cavity 854 is provided between the bottom of the well 852 and the membrane 824. The cavity 854 has an opening in communication with the outside on a side wall of the container portion 850 so that air can be introduced into the cavity 854 through the opening.

When a contact lens and the like are tested using the test device 810, the cells α are seeded and cultured on the membrane 824 to allow the cells α to adhere onto the membrane 824 (the step S110). Air is then introduced into the cavity 854 to expand the cavity 854. As a result, as shown in FIG. 12B, the membrane 824 having the cells α on the surface thereof expands into a substantially hemispherical shape which is convex toward the vertically upward direction (in the −X direction). At this time, an annular plate having an inner diameter comparable with the diameter of the contact lens 60 may be placed, for example, on the outer peripheral portion of the membrane 824 so that the membrane 824 can expand into a shape which can be brought into contact with the contact lens 60. The cavity 854 filled with air when the membrane 824 expands hemispherically as described above may serve as a portion for supporting the contact lens 60 on the concave side, and may also be referred to as a "supporting portion."

Then, the upper jig 840 having the contact lens 60 attached is inserted into the well 852. The upper jig 840 is a substantially hollow cylindrical member having an outer diameter smaller than the inner diameter of the container portion 850, and configured so that the contact lens 60 can be attached to the end portion in the vertically downward direction (in the +X direction) with the convex side oriented toward the vertically upward direction (in the −X direction). The contact lens 60 may be attached to the upper jig 840 by, for example, providing an engaging portion configured to enable the outer peripheral portion of the contact lens 60 to engage with the upper jig 840. By further pushing down the upper jig 840 from a state shown in FIG. 12C, the membrane 824 on which the cells α are adhered to can be brought into close contact with the concave side of the contact lens 60. This configuration can also produce similar effects as the first embodiment.

J. Other Embodiments

In each of the above embodiments, the convex portion 44 of the upper jig 40 or the convex portion 232 of the lower jig 230 which support the contact lens 60 from the concave side is configured to protrude hemispherically. However, a different configuration may be used. For example, in a case where a convex portion is brought into contact with the contact lens 60 as in the test device 10 according to the first embodiment, the test device 210 according to the third embodiment, the test device 410 according to the fifth embodiment, the test device 510 according to the sixth embodiment, the test device 610 according to the seventh embodiment, and the test device 710 according to the eighth embodiment, the shape of the convex portion may be configured so as to be in contact with only a portion of the concave side of the contact lens 60. This configuration also enables the contact lens 60 to be brought into close contact with the membrane 24 by pressing the contact lens 60 against the membrane 24. In this case, the shape of a cross-section perpendicular to the X direction at the above convex portion is preferably configured as a shape that enables a pressing force to be evenly applied to the contact lens 60, such as as a cruciform shape where the central axis O of a test device passes through the center.

In a test device which is to be used in a test of a contact lens and the like, the concave side of the contact lens 60 is preferably supported by a supporting portion, but a different configuration may be used. For example, in a case where the contact lens 60 has sufficient strength, a supporting portion needs not be arranged at the concave side of the contact lens 60.

In each of the above embodiments, the annular supporting base 22 of the membrane member 20 is configured to be a sheet-shaped member, but a different configuration may be used. For example, the supporting base 22 may be tubular, extending in the X direction. However, the annular supporting base 22 is preferably configured to be a sheet-shaped (ring-shaped) member where a constraint force against the membrane 24 may be smaller. This is because this configuration can prevent insufficient deformation due to the stiffness of the supporting base 22 when the membrane 24 in a swollen state undergoes deformation along the contact lens 60.

The present disclosure shall not be limited to the aforementioned embodiments, and can be implemented in various forms without departing from the spirit of the present disclosure. For example, technical features in the embodiments corresponding to those in the aspects described in the section SUMMARY may be suitably replaced or combined to solve a part of or all of the aforementioned problems, or to achieve a part of or all of the aforementioned effects. Further, a technical feature herein may be suitably deleted if it is not described as essential.

The present disclosure may be implemented as the following aspects.

(1) According to one aspect of the present disclosure, provided is a test method performed using a lens which comes into contact with a human body during use. The above test method comprises: providing a membrane member including a membrane swellable upon absorbing water and a supporting base having an annular shape to support an outer periphery of the membrane; allowing cells to adhere onto the membrane of the membrane member; and bringing the membrane to which the cells are adhered into close contact with a surface of the lens, by immersing the membrane member and the lens into a liquid and deforming the membrane in a swollen state along the surface of the lens.

The test method according to this aspect ensures a larger contact area with cells used for tests, leading to an increased sensitive of safety tests performed using a lens, as well as increased validity of test results.

(2) In the test method according to the above aspect, a side of the membrane to which the cells are adhered may be brought into close contact with the surface of the lens when the membrane to which the cells are adhered is brought into close contact with the surface of the lens. According to the test method of this aspect, the lens is tested under conditions closer to those under which the lens would be used on a human body.

(3) In the test method according to the above aspect, the membrane may have a plurality of through holes formed to pass through the membrane in a thickness direction, and a back side of the a of the membrane to which the cells are adhered may be brought into close contact with the surface of the lens when the membrane to which the cells are adhered is brought into close contact with the surface of the lens. According to the test method of this aspect, a larger contact area with the cells is ensured on the lens even when a test is performed according to an aspect in which the cells are brought into contact with the lens via the through holes of the membrane.

(4) In the test method according to the above aspect, the liquid may include a component contained in a medium for culturing the cells. According to the test method of this aspect, the cells are maintained in better conditions to perform the test.

(5) In the test method according to the above aspect, a concave side of the lens may be supported by a supporting portion when the membrane to which the cells are adhered is brought into close contact with the surface of the lens. According to the test method of this aspect, deformation of the lens is controlled, and thus the adhesion of the lens with the membrane is improved.

(6) In the test method according to the above aspect, the membrane may be arranged between the supporting portion and the concave side when the membrane to which the cells are adhered is brought into close contact with the surface of the lens. According to the test method of this aspect, the lens is tested under conditions closer to those under which the lens would be used on a human body.

(7) In the test method according to the above aspect, the membrane may be arranged on a convex side of the lens when the membrane to which the cells are adhered is brought into close contact with the surface of the lens. According to the test method of this aspect, a side which is different from one to be brought into contact with the eye ball during use is also tested accurately.

(8) In the test method according to the above aspect, the method may include a step of culturing the cells in a test liquid including an agent which is to be used along with the lens while the membrane maintains close contact with the surface of the lens. According to the test method of this aspect, the agent which is to be used along with the lens is tested under conditions closer to those under which the lens would be used on a human body.

(9) in the test method according to the above aspect, the membrane may have an area swelling rate of not be less than 1%. According to the test method of this aspect, the membrane is easily brought into close contact with the lens.

(10) In the test method according to the above aspect, the membrane may have an area swelling rate of not be less than 3%. According to the test method of this aspect, the membrane is more easily brought into close contact with the lens.

(11) In the test method according to the above aspect, the membrane may have an area swelling rate of not be less than 5%. According to the test method of this aspect, the membrane is even more easily brought into close contact with the lens.

(12) In the test method according to the above aspect, the membrane may have a dry membrane thickness of 1 to 100 µm. According to the test method of this aspect, the membrane is more easily brought into close contact with the lens.

(13) In the test method according to the above aspect, the membrane may be a polyurethane membrane. According to the test method of this aspect, the membrane is more easily brought into close contact with the lens, and the cells is more easily cultured on the membrane.

The present disclosure may also be implemented in various forms other than test methods. For example, it may be implemented in a form such as a test device and the like for a test performed using a lens which comes into contact with a human body during use.

What is claimed is:

1. A test method performed using an ocular lens which comes into contact with an eye during use, the test method comprising:
   providing a membrane member including a membrane swellable upon absorbing water and a supporting base having an annular shape to support an outer periphery of the membrane, wherein the membrane becomes stretchable as the membrane is softened when the membrane swells upon absorbing water, and an area swelling rate of the membrane is 1% or more;
   allowing cells to adhere onto the membrane of the membrane member;
   bringing the membrane to which the cells are adhered into close contact with a surface of the ocular lens, by immersing the membrane member and the ocular lens into a liquid and deforming the membrane in a swollen state along the surface of the ocular lens; and
   testing the ocular lens that has been immersed in the liquid.

2. The test method according to claim 1, wherein
   when the membrane to which the cells are adhered is brought into close contact with the surface of the ocular lens, a side of the membrane to which the cells are adhered is brought into close contact with the surface of the ocular lens.

3. The test method according to claim 1, wherein
   the membrane has a front side to which the cells are adhered and an opposing back side,
   the membrane has a plurality of through holes formed to pass through the membrane in a thickness direction, and
   when the membrane to which the cells are adhered is brought into close contact with the surface of the ocular lens, the back side of the membrane is brought into close contact with the surface of the ocular lens.

4. The test method according to claim 1, wherein
   the liquid includes a component contained in a medium for culturing the cells.

5. The test method according to claim 1, wherein
   when the membrane to which the cells are adhered is brought into close contact with the surface of the ocular lens, a concave side of the ocular lens is supported by a supporting portion.

6. The test method according to claim 5, wherein
   when the membrane to which the cells are adhered is brought into close contact with the surface of the ocular lens, the membrane is arranged between the supporting portion and the concave side.

7. The test method according to claim 5, wherein
   when the membrane to which the cells are adhered is brought into close contact with the surface of the ocular lens, the membrane is arranged on a convex side of the ocular lens.

8. The test method according to claim 1, further comprising:
   culturing the cells in a test liquid including an agent which is normally to be used along with the ocular lens when the ocular lens is in use on an eye while the membrane maintains close contact with the surface of the ocular lens.

9. The test method according to claim 1, wherein
   the membrane has an area swelling rate of not less than 3%.

10. The test method according to claim 1, wherein
    the membrane has an area swelling rate of not less than 5%.

11. The test method according to claim 1, wherein
    the membrane has a dry thickness of 1 to 100 µm.

12. The test method according to claim 1, wherein
    the membrane is a polyurethane membrane.

13. A test method performed using an ocular lens which comes into contact with an eye during use, the test method comprising:
    providing a membrane member including a membrane swellable upon absorbing water and a supporting base having an annular shape to support an outer periphery of the membrane;
    allowing cells to adhere onto the membrane of the membrane member;
    bringing the membrane to which the cells are adhered into close contact with a surface of the ocular lens by immersing the membrane member and the ocular lens into a liquid and deforming the membrane in a swollen state along the surface of the ocular lens, the membrane sized and constructed to be in close contact with substantially the entire surface of the ocular lens, wherein when the membrane to which the cells are adhered is brought into close contact with the surface of the ocular lens, a side of the membrane to which the cells are adhered is brought into close contact with the surface of the ocular lens; and
    testing the ocular lens that has been immersed in the liquid.

* * * * *